United States Patent [19]

Niitsu et al.

[11] Patent Number: 5,843,677
[45] Date of Patent: Dec. 1, 1998

[54] METHOD OF ASSAYING ASIALOGLYCOPROTEIN RECEPTOR AND ASSAY REAGENT THEREFOR

[75] Inventors: Yoshiro Niitsu, Sapporo; Yutaka Kohgo, Asahikawa; Junji Kato, Sapporo; Hirokazu Yago, Tokyo; Hisashi Hanada, Tokyo; Koji Ushizawa, Tokyo, all of Japan

[73] Assignee: Daiichi Pure Chemicals Co., Ltd., Tokyo, Japan

[21] Appl. No.: 722,153

[22] PCT Filed: Apr. 19, 1995

[86] PCT No.: PCT/JP95/00770

§ 371 Date: Oct. 18, 1996

§ 102(e) Date: Oct. 18, 1996

[87] PCT Pub. No.: WO95/29403

PCT Pub. Date: Nov. 2, 1995

[30] Foreign Application Priority Data

Apr. 20, 1994 [JP] Japan .................................. 6-081268

[51] Int. Cl.⁶ ............................ G01N 33/53; C07K 16/28
[52] U.S. Cl. ........................ 435/7.1; 435/7.2; 435/7.21; 435/7.9; 530/387.1; 530/388.22; 530/388.85; 530/389.1; 530/391.1; 530/391.3
[58] Field of Search .............................. 435/7.9, 7.1, 7.2, 435/7.21; 530/387.1, 388.22, 388.85, 389.1, 391.1, 391.3

[56] References Cited

U.S. PATENT DOCUMENTS 4,764,468  8/1988  Wehner et al. ......................... 435/188
4,828,983  5/1989  McClune .................................. 435/17

FOREIGN PATENT DOCUMENTS 147368  4/1981  U.S.S.R. .

OTHER PUBLICATIONS

Kohgo Y. et al. 1993. Hybridoma 12(5): 591–598.
Whittaker, R.G. et al. 1983. J. Sci. Food Agric. 34(10):1143–48.
Morohoshi, N et al. 1989. Bull Sep For Tokyo Univ. Agric. Technol 6(26): 69–78.
Anonymous, Oct. 10, 1990–RD 318067.

*Primary Examiner*—Toni R. Scheiner
*Assistant Examiner*—Nancy A. Johnson
*Attorney, Agent, or Firm*—Oblon, Spivak, McClelland, Maier & Neustadt, P.C.

[57] ABSTRACT

The present invention is directed to a method of immunoassay of asialoglycoprotein receptors (AGPR) by bringing a specimen into contact with a monoclonal antibody that recognizes AGPR, wherein the pH of a diluted specimen solution is adjusted from 5 to 7 or phenol is added to a solution of an enzyme-labeled antibody. This method is excellent in the sensitivity and accuracy of AGPR assay and can be applied also to the screening of hepatopathy remedies.

15 Claims, 2 Drawing Sheets

METHOD OF ASSAYING ASIALOGLYCOPROTEIN RECEPTOR AND ASSAY REAGENT THEREFOR

TECHNICAL FIELD

The present invention relates to a method for measuring concentration of asialoglycoprotein receptors (hereinafter collectively referred to as "AGPR"), which is useful in the diagnosis of the functions of hepatocytes with improved sensitivity and accuracy. The invention also relates to a reagent used in the method and to a method for screening therapeutic drugs employing the method.

BACKGROUND ART

The liver is the largest parenchymatous organ in the human body and plays a central role in metabolism. Its main functions are diversified and include: (1) intermediary metabolism in relation to nutrients; i.e., oxidation of substances such as saccharides, fatty acids, and amino acids that are absorbed intestinally or mobilized from the peripheral tissue, as well as gluconeogenesis, synthesis and storage of lipids and proteins, and supply of lipids and proteins to other organs and peripheral tissues; (2) metabolism of various proteins other than nutrients and of precursors of such proteins; e.g., synthesis of constituent proteins of body tissue, serum proteins, and a variety of enzymes related to metabolism in the liver; (3) detoxication, conjugation, destruction, and deactivation of exogenous drugs, intrinsic hormones, ammonia, etc.; (4) intake and excretion as reticuloendothelial functions; (5) excretion and digestive functions associated with the production of bile; and (6) maintaining the internal environment by metabolism of water, electrolytes, and vitamins. Accordingly, lesions in the liver cause systemically abnormal metabolism, which induces secondary disorders in other organs to affect the body generally. Therefore, it is very important to know liver functions in morbid livers.

In the meantime, with recent advancement in medical equipment, progress of hepatectomy, and development of liver preserving fluids and immunosuppressants, hepatectomy in cases of liver carcinoma and liver transplantation in cases of hepatic cirrhosis have come to be performed actively. Therefore, grasping of liver functions is critical after surgery.

Hitherto, "standards for the selection and combination of liver function tests"—which were suggested by the liver function study group of the Japan Digestive System Disease Society as biochemical clinical test items for investigating liver functions (Nisshokai-shi, Vol. 85, pp. 1210–1214, 1988) have been widely used by internists and surgeons.

In the field of surgery, Ozawa et al. demonstrated that evaluation of the function of liver mitochondria in a noninvasive and more direct manner; i.e., using the ketone body ratio in arterial blood (AKBR), is an excellent liver function test (Gastroenterology, Vol. 76, pp. 691–696, 1979).

However, conventional biochemical test items tend to have low liver specificity and are frequently influenced by factors external to the liver. Moreover, in the method employing AKBR, care must be taken in collection of blood, handling of specimens, measurement, and in interpretation of data; thus this method cannot be said to be a suitable method. In spite that estimation of the post operational prognosis is important in consideration of high frequency of onset of post-operational liver disorders, a suitable test method has not yet been discovered.

In the field of internal medicine, Niitsu et al. reported that assay of asialoglycoprotein receptors (AGPR), which are highly specific to the liver, is suitable for use in the diagnosis of liver diseases (Japanese Patent Application Laid-Open (kokai) No. 4-356198).

AGPR is a lectin that recognize galactose and N-acetylgalactosamine residue (Morell et al., J. Biol. Chem., vol. 246, pp. 1461–1467, 1971). It is a liver-specific transmembrane glycoprotein which is present on the surface of the cell membrane of the liver parenchyma (Matsuura et al., J. cell Biol., Vol 95, pp. 864–875, 1982). Moreover, as a result of research using $^{125}$I-labeled asialoorosomucoid, which is a ligand of AGPR, the amount of AGPR on the surface of the cell membrane of the liver parenchyma has been found to decrease in relation to the degree of severity of hepatic disorders (Sawamura et al., Gastroenterology, Vol. 87, pp. 1217–1221, 1984).

However, conventional methods of assaying AGPR are not completely satisfactory when quantitative measurement of AGPR in a specimen is desired, and therefore, it has been difficult to properly diagnose liver diseases.

In the screening for safe and effective remedies, effects of the remedies on cultures of target cells or cultures of liver cells have conventionally been determined based on functional disorders and functional recovery of such cells. However, functions of liver cells cannot be said to be fully understood by the examination of only substance production ability, metabolism, detoxication activities, and similar functions of liver cells, though effects of remedies on cultures of liver cells have heretofore been determined based on the results of such examination. Therefore, in the development of new remedies, a simple method has still been desired so as to identify changes in cell membranes, endocytosis, etc. which are functions different from those mentioned above.

Thus, in view of a need to establish a method of assaying AGPR in order to determine functions of liver cells, the applicant of the present invention has previously discovered a method for assaying AGPR using a monoclonal antibody, and has applied for a patent (Japanese Patent Application Laid-Open (kokai) No. 4-356198). Yet, development of a method for assaying AGPR with higher sensitivity and improved accuracy is still desired.

Accordingly, an object of the present invention is to provide a method for assaying AGPR with high sensitivity and enhanced accuracy, as AGPR is effective for grasping liver functions particularly regenerating ability of the liver, detecting alcohol-induced liver disorders, and determining the effect of remedies or the effect on liver cells of remedies.

DISCLOSURE OF THE INVENTION

In view of the foregoing, the inventors of the present invention conducted careful studies, and found that in an immunoassay in which a specimen is brought into contact with a monoclonal antibody that recognizes AGPR, if the pH of a diluted specimen solution is adjusted to 5 to 7 or phenol is added to a solution of an enzyme-labeled antibody, AGPR can be assayed with high sensitivity and with enhanced accuracy. Moreover, the present inventors found that screening of remedies can be easily performed using this method and by assaying AGPR released by cultured liver cells and present in a culture supernatant. The present invention was accomplished based on these findings.

Accordingly, the present invention provides a method of immunoassay of AGPR by bringing a specimen into contact with a monoclonal antibody that recognizes AGPR, characterized in that the pH of a diluted specimen solution is adjusted to 5 to 7.

The present invention also provides a method of immunoassay of AGPR by bringing a specimen into contact with a monoclonal antibody that recognizes AGPR, characterized in that phenol is added to a solution of an enzyme-labeled antibody.

The present invention also provides a method of immunoassay of AGPR by bringing a specimen into contact with a monoclonal antibody that recognizes AGPR, characterized in that phenol is added to a solution of an enzyme-labeled antibody and that the pH of a diluted specimen solution is adjusted from 5 to 7.

The present invention also provides a method of screening remedies, characterized in that the amount of asialoglycoprotein receptors released from liver cells and present in a culture supernatant is determined using the above-mentioned method of the immunoassay of AGPR of the present invention.

Furthermore, the present invention provides a reagent for assaying AGPR, the reagent comprising phenol and a monoclonal antibody that recognizes AGPR.

BEST MODE FOR CARRYING OUT THE INVENTION

The monoclonal antibody that recognizes AGPR and is used in the present invention (hereinafter referred to as "anti-AGPR monoclonal antibody") may be prepared, for example, by the following method.

The AGPR, which serves as an antigen, may be prepared from human autopsied liver according to a known method; e.g., a method of Baenzinger et al. (Journal of Bio. Chem., Vol. 255, 4607–4613, 1980). Briefly, human liver autopsied with informed consent is homogenized, and liver cell membrane fractions are centrifugally separated. To one volume of the obtained fractions, about 9 volumes of cold acetone are added. By filtration, insoluble matter is recovered in the form of acetone powder. AGPR is extracted from the acetone powder throguh use of a buffer that contains a surfactant. Calcium chloride is added to the resultant extract, and the mixture is subjected to affinity chromatography using D-galactose—agarose gel, to thereby obtain purified AGPR.

The anti-AGPR monoclonal antibody may be prepared using the above-described AGPR as an immunogen and a known technique for cell fusion. Briefly, AGPR is emulsified in Freund's complete adjuvant or in an adjuvant that is formed of a trehalose dimycolic acid and low-toxic lipid A at an optimum concentration (Ribi adjuvant system). The thus-prepared emulsion is administered several times to a mouse intraperitoneally, subcutaneously, or intravenously every several weeks, to thereby immunize the mouse. When a certain period has elapsed, spleen cells of the mouse are removed, and are then subjected to a polyethylene glycol treatment together with mouse myeloma cells having a suitable marker such as hypoxanthine-guanine-phosphoribosyltranspherase deficiency (HGPRT$^-$) or thymidine kinase deficiency (TH$^-$), to thereby obtain a variety of hybridoma cells. From these cells, hybridomas that produce anti-AGPR monoclonal antibodies can be screened out based on the reactivity to AGPR of antibodies produced in a culture supernatant of the hybridoma cells. In order to obtain single clones of the target hybridoma, the hybridomas are seeded in the number of 1–10 per well in the wells of a 96-well microtiter plate, in which normal spleen cells or thymus cells have been seeded in advance in the number of $10^6$ cells per well so as to form a feed layer. The growing clones are again subjected to a screening step (subscreening). Subscreening is repeated to obtain hybridoma cell lines.

The medium for culturing hybridomas is not particularly limited, and any medium that is suitable for this purpose may be used. Preferably, a medium prepared by incorporating fetal calf serum, L-glutamine, L-pyruvic acid, and antibiotics (penicillin G and streptomycin) in RPMI 1640 may be used. Culturing is preferably performed, for example, in a $CO_2$ concentration of 5 wt % (hereinafter simply referred to as %), at 37° C., for 3 days.

Through an animal cell culturing technique or a culturing technique within the abdominal cavity of a mouse using the above-selected hybridomas, there is obtained a culture supernatant or mouse ascites, which is then subjected to salt precipitation, column chromatography using an ion exchange resin and a molecular sieve gel, or affinity chromatography using protein A and protein G, to thereby purify monoclonal antibodies. The specificity of the resultant monoclonal antibodies may be confirmed, for example, through a Western blotting method.

In order to quantitatively determine the amount of AGPR in a human specimen, an immunoassay is performed using one or more kinds of the thus-obtained anti-AGPR monoclonal antibodies. Exemplary immunoassay methods include, for example, an Ouchterlony method, a one-dimensional diffusion method, immunonephelometry, enzyme immunoassay, latex immunoassay, radioimmunoassay, and fluoroimmunoassay. When enzyme immunoassay is performed, any species of anti-AGPR monoclonal antibodies are immobilized onto an insoluble carrier in a suitable buffer, and the resultant insoluble antibodies are allowed to react with a specimen in the presence of another species of enzyme-labeled anti-AGPR monoclonal antibodies, which are also allowed to react with the specimen. By measuring the activity of the enzyme bound to the second antibody, amounts of human AGPR can be determined.

Examples of insoluble carriers which may be used include a variety of synthesized polymers such as polystyrene, polyethylene, and polypropylene; glass; silicones; and insoluble polysaccharides (e.g., cross-linked dextran, polysaccharides). These carriers may take the form of spheres, rods, or fine particles. Also, they may be used in the form of test tubes or microplates. When insoluble antibodies are prepared on spheres, rods, test tubes, or microplates, the antibody concentration is preferably between 1 and 10 μg/ml; whereas when they are prepared on fine particles, the antibody concentration is preferably between 1 and 10 mg/ml. Buffers which may be used fall in the range from weakly acidic to alkaline, and exemplary buffers include phosphate buffer, glycine buffer, carbonate buffer, and Tris buffer. The reaction time for preparing insoluble antibodies is preferably between 1 and 72 hours, and the reaction is preferably carried out at room temperature or at 4° C.

A detergent liquid used for subsequent washing is preferably phosphate buffer (5–100 mM) or Tris buffer, which are weakly acidic, neutral, or weakly basic with pH falling in the range between 6 and 8. In order to avoid nonspecific reactions, it is preferred that there be added 50–200 mM of NaCl or KCl; or 0.01–0.1% surfactants such as Tween 80, Tween 20, or NP-40. It is also possible to add 0.1–5 mM of a chelating agent (e.g., EDTA), so as to eliminate inhibitors of enzymatic reactions.

Enzyme-labeled antibodies which are used in the present invention may be prepared by known methods. For example, they may be prepared through a method described by Nakane et al. (Nakane, P. K. et al., J. Histochem Cytochem, 22, 1084–1089, 1984) or through a method described by Ishikawa et al. method (a maleimide method; "Enzyme Immunoassay," 3rd ed., published by Igaku-shoin). In these methods, non-fragmented immunoglobulin molecules are used in their intact forms, or if needed, F(ab')$_2$ or Fab' is first obtained by partial lysing of antibodies using a suitable protease, and is then labeled with an enzyme. Examples of enzymes used for labelling include peroxidase, alkaline phosphatase, β-D-galactosidase, and glucose oxidase.

The composition of enzyme-labelled antibody solutions may be suitably determined in accordance with the antigen bound to a solid antibody and the enzyme-labeled antibody so as to be adapted to suitable reaction conditions (pH, buffers, proteins, salts, surfactants, etc.). For example, buffer concentration and pH may be as follows: 10–500 mM (particularly 10–50 mM) of phosphate buffer, Tris buffer, and Good's buffer (e.g., MES·BisTris·ACES·BES·HEPES); weakly acidic to weakly basic pH range between 6 and 8 (particularly between 6.5 and 7.5).

In the present invention, it is preferred that phenol be added in an amount of 0.001 to 0.2%, preferably 0.01 to 0.1%, so as to accelerate the reaction and stabilize the labeled antibody.

For the purposes of elimination of non-specific reactions and stabilization, the enzyme-labeled antibody solution preferably contains proteins such as BSA, low-fat milk, or gelatin in amounts of 0.1–10%, particularly preferably 0.1–0.5%; electrolytes such as NaCl and potassium chloride in amounts of 20–1,000 mM, particularly preferably 50–200 mM; or surfactants such as Tween 80, Tween 20, and NP-40 in amounts of 0.01–0.1%.

If the labeling substance is an enzyme, a substrate—together with a color developer if needed—is used so as to determine the enzyme's activity. When the enzyme is peroxidase, the substrate may be hydrogen peroxide, and the color developer may be o-phenylenediamine, 3,3',5,5'-tetramethylbenzidine, or 2,2'-azinodi-(3-ethylbenzthiazolinesulfonic acid) ammonium salt; when the enzyme is alkaline phosphatase, the substrate may be p-nitrophenylphosphate, 3-(4-methoxyspiro{1,2-dioxetane-2',3-tricyclo-[3.3.1.1$^{3,7}$]decane-4-yl) phenylphosphate:AMPPD; when the enzyme is β-D-galactosidase, the substrate may be β-D-galactopyranoside or 4-methylunbelliferyl-β-D-galactopyranoside; and when the enzyme is glucose oxidase, the substrate may be β-D-glucose and the color developer may be peroxidase, with both used in the co-presence of peroxidase.

The pH of diluted specimen solutions which are used in the present invention must fall in the range between 5 and 7, and preferably between 5.5 and 6.5. When pH is lower than 5 or greater than 7, measurement sensitivity decreases, which is not preferred. The composition of diluted specimens is suitably determined using buffers in accordance with the nature of the immobilized antibody and the nature of the antigen within the above-mentioned pH range. Examples of buffers which may be used include 20–500 mM (preferably 50–200 mM) of citric buffer, maleic buffer, phosphate buffer, and Good's buffer (e.g., MES·BisTris·ACES·BES). For the purposes of elimination of non-specific reactions and stabilization, it is recommended that three be added proteins such as BSA, low-fat milk, or gelatin in amounts of 0.1–10%, (preferably 1–5%); electrolytes such as NaCl and potassium chloride in amounts of 20–1,000 mM (preferably 50–200 mM); and surfactants such as Tween 80, Tween 20, and NP-40 in amounts of 0.01–0.1%.

The immunoreaction is carried out via a first reaction and a second reaction. In the first reaction, a specimen is brought into contact with insoluble antibodies so as to cause antigens in the specimen to bind to the antibodies, to thereby form insoluble antibody-antigen complexes. In the second reaction, enzyme-labeled antibodies are bound to the complexes, to thereby form insoluble antibody-antigen-enzyme-labeled antibody complexes. When the enzyme activity of the thus-obtained complexes is measured, the amount of antigens in the specimen (human AGPR) can be determined.

In the present invention, if phenol is incorporated into the enzyme-labeled antibody solution and the pH of the diluted specimen solution is adjusted to fall within the range of 5–7, the AGPR concentration can be determined with higher sensitivity and improved accuracy.

Screening of remedies by the use of the above-described method for assaying AGPR is performed as follows. A primary culture of liver cells, liver cell strains, or liver cells that have been damaged with a chemical, etc. may be used, and substances released from the liver cells into a supernatant—or substances contained in the liver cells—are compared in terms of the presence or absence of the drug to be screened. For example, through measurement of the amount of AGPR present in a culture supernatant (both serum-containing and serum-free media may be used), it is possible to determine the fluidity of membranes in the state where liver cells are active; i.e., turnover of cytoplasm substances and intracellular mechanism associated with endocytosis.

EXAMPLES

The present invention will next be described in more detail by way of examples, which should not be construed as limiting the invention.

Referential Example 1

Purification of AGPR

A human liver autopsied with informed consent (obtained from a patient who had succumbed to gastric cancer) was minced (180 g). The minced liver tissue was washed with 5 mM EDTA and with 1 mM phenylmethylsulfonylfluoride-containing 50 mM Tris-HCl buffer (hereinafter referred to as Tris-HCl, pH 7.8, washing liquid 1), and then homogenized with a polytron blender containing 900 ml of washing solution 1. The resultant suspension was subjected to centrifugal separation at 800×g for 10 minutes. The supernatant was centrifuged at 100,000×g for 90 minutes. The pellet was resuspended in purified water, and cold acetone was added thereto in a volume of 9 times that of the pellet. Acetone powder was recovered through filtration. The recovered acetone powder (20 g) was washed with Tris-HCl (20 mM, pH 7.8) that contained 0.2M NaCl, and then extracted with 300 ml of Tris-HCl (20 mM, pH 7.8) that contained 0.4M KCl and 1% Triton X-100. The extract was centrifuged at 1,200×g for 15 minutes, the supernatant was recovered, and CaCl$_2$ was added so as to adjust the final concentration to 25 mM. AGPR adsorbed onto a D-galactose-agarose gel was eluted with 20 mM ammonium acetate that contained NaCl (1.25M)(pH 5.1), to thereby purify AGPR. The purity of the thus-purified AGPR was approximately 90%. The protein concentration determined by a modified method based on Lowry method was 130 μg/ml.

Referential Example 2
Preparation of Monoclonal Antibodies
(1) Immunization

AGPR purified in Referential Example 1 was used for immunization (20 μg/immunization). Freund's complete adjuvant was used in the first immunization, and a 1:1 mixture of Freund's complete adjuvant and incomplete adjuvant was used as a booster. AGPR (100 μl) and Freund's adjuvant (100 μl) were mixed, and the resultant emulsion (200 μl) was intraperitoneally injected to a male BALB/c mouse. This immunization procedure was repeated every 2 weeks for a total of 4 times.

In addition to the above-mentioned immunization using Freund's adjuvant, immunization was also performed using a modified method based on a Ribi adjuvant system commercially available from Funakoshi. An emulsion for performing immunization for this purpose was prepared as follows. A Potter homogenizer was used. Purified AGPR (20 μg) was placed in a grinder tube and was brought to dryness by the application of nitrogen gas. A mixture of monophosphate lipid A (MPL) and trehalose dimicolic acid (TDM) in a mixture of chloroform and methanol (4:1) was then added, and the resultant mixture was then dried by the application of nitrogen gas. Squalene (4 μl) was added to the tube. The mixture of antigen, adjuvant, and squalene was mixed for 3 minutes at 1,200 rpm using a Teflon rod secured to a three-one motor. Thereafter, 13 mM phosphate buffer (pH 7.2, 200 μl) containing 0.2% Tween 80 and 0.72% NaCl was added and the mixture was mixed at 1,200 rpm for 4 minutes, to thereby obtain an emulsion for immunization. The thus obtained emulsion (200 μl) was intraperitoneally injected to a BALA/c mouse. This immunization procedure was repeated every 2 weeks for a total of 4 times.

In the first immunization, 50 μg of TDM and 50 μg of MPL were used, and in a booster, 50 μg of TDM and 5 μg of MPL were used.

Blood was collected from the ocular fundus vein of the mice immunized by the above-described two methods, and the antibody titer was determined by ELISA. Cells of a mouse that exhibited a higher titer were used for cell fusion.

(2) Cell Fusion

One month after the 4th immunization, purified AGPR (20 μg) diluted in 200 μl of physiological saline was intraperitoneally injected to a mouse. The spleen was removed from the mouse 3 days thereafter. In an RPMI 1640 medium, the removed spleen was thoroughly loosened on a slide glass using a pincette, to thereby recover spleen cells. The recovered cells were centrifuged at 1,500 rpm for 5 minutes, and the obtained cells were washed with the same medium and centrifuged. Finally, the same medium (2 ml) containing 15% fetal calf serum (FCS) was added so as to prepare a spleen cell suspension. Acridine orange/ethidium bromide solution (0.1 mg of each was dissolved in 1 ml of PBS) and the suspension were mixed at a proprtion of 1:1, and the resultant mixture was placed under a fluorescent microscope, and the number of live spleen cells was counted. A total of $10^8$ live spleen cells and $10^7$ preincubated mouse myeloma cells SP2/O-Ag14 in the logarithmic growth phase were mixed, and subsequently centrifuged at 1,500 rpm for 5 minutes. After the supernatant was removed, the cells were thoroughly loosened and suspended in a GKN solution (a solution of 8 g NaCl, 0.4 g KCl, 2 g glucose, 1.41 g $Na_2HPO_4$, and 0.78 g $NaH_2PO_4\cdot 2H_2O$ in 1 liter of purified water). The suspension was centrifuged at 1,500 rpm for 5 minutes, to thereby wash the cells. After repeated washings, 0.5 ml of a GKN solution containing 50% (w/v) polyethylene glycol 1540 was added, and the mixture was gently stirred for 1 minute. A GKN solution (10 ml) was gradually and gently added thereto, to thereby stop the reaction. The reaction was centrifuged at 1,500 rpm for 5 minutes. The obtained cells were suspended in RPMI 1640 (30 ml) containing 15% FCS, and 0.1 ml of the suspension was dispensed into each well of three 96-well microculture plates containing an HAT medium (an RPMI 1640 medium containing $10^{-4}$M hypoxanthine, $4\times10^{-7}$M aminopterin, 1.5× $10^{-5}$M thymidine, and 15% FCS) and feeder cells (200 μl per well). The cells were incubated at 37° C. in a 5% $CO_2$ incubator. On day 10 of incubation, propagation of fused cells was confirmed in all wells.

(3) Selection of Anti-AGPR Antibody-Producing Hybridomas and Cloning

The presence or absence of anti-AGPR antibodies in the culture supernatant was determined by ELISA. That is, screening was performed using a 96-well microplate to which purified AGPR had been immobilized. In detail, AGPR was diluted with 13 mM phosphate buffer (pH 7.2; PBS) containing 0.72% NaCl, so as to adjust the AGPR concentration to 0.2 μg/ml. The solution was dispensed into a 96-well microplate, in an amount of 50 μl/well, and was allowed to stand overnight at 4° C. Subsequently, the microplate was washed three times with PBS (pH 7.2; BSA-PBS) containing 1% bovine serum albumin and 0.05% Tween 20. Fifty μl of the culture supernatant were added to each well of the plate, and the microplate was warmed to 37° C. for 1 hour. Thereafter, the microplate was washed three times with PBS, and to the microplate was added 50 μl of 1,000-fold diluted peroxidase-labeled anti-mouse IgG antibody (specific to the Fc site, derived from goat) using BSA-PBS for dilution. The microplate was warmed to 37° C. for 1 hour, and washed five times with PBS. Citrate-phosphate buffer (pH 5.0) containing orthophenylenediamine (11 mM) and 0.02% hydrogen peroxide water was added to the wells of the microplate in an amount of 50 μl/well, to thereby cause a reaction. The reaction was allowed to proceed for 30 minutes at room temperature, and was subsequently stopped by the addition of 4.5M sulfuric acid in an amount of 50 μl/well. The specimens that exhibited high levels of absorbance at 550 nm were selected.

The cells that presented positive results in ELISA were checked by Western blotting for reactivity with AGPR derived from other animals, and monoclonal antibodies that cross-reacted were selected. Briefly, in accordance with the above-mentioned purification procedure of AGPR, acetone powder was prepared from the livers of a rabbit, a rat (SD), and a mouse (BALB/c), and their extracts were independently applied to wells of 4–20% SDS-PAGE in an amount of 10 μl/well. These samples were electrophoresed, and then transcribed onto a polyvinylidene difluoride (PVDF) membrane by means of semi-dry blotting at 80 mA for 1 hour using buffers (Anode solution 1:0.3M Tris and 20% methanol; Anode solution 2:25 mM Tris and 20% methanol; and Cathode solution 1:25M Tris, 40 mM ε-amino-n-caproic acid, and 20% methanol). The PVDF membrane was blocked overnight at 4° C. with PBS that contained 10% skim milk. Thereafter, the respective monoclonal antibodies obtained this time were reacted therewith. The transcription membrane was cut into strips, and each strip was allowed to react with 500 μl of a culture supernatant of each hybridoma for 1 hour at room temperature. The product of reaction was washed three times with PBS that contained 0.05% Tween 20 (PBST), and was then allowed to react with 500 μl of a 200-fold dilution of biotin-labeled anti-mouse IgG horse antibody (diluted with PBS containing 1% horse serum) at room temperature for 1 hour. The product of reaction was washed three times with PBST, and was then subjected to an enzymatic reaction by the addition of a substrate solution containing 50 mM Tris-HCl (pH 7.6, 100 ml), diaminobenthidine (25 mg), and hydrogen peroxide (20 µl). As soon as any band was confirmed, the reaction was stopped by the application of water for washing.

The results are shown in Table 1. It was confirmed that the obtained monoclonal antibodies not only reacted with human AGPR, but also cross-reacted with AGPRs originating from other animals.

centrifuged at 3,000 rpm for 10 minutes, to thereby remove insoluble matter such as cells. An equivalent volume of saturated ammonium sulfate solution was added to the supernatant while stirring, and the mixture was allowed to stand overnight at 4° C. The pellet was recovered by centrifugal separation, dissolved in 20 mM Tris-HCl buffer (pH 8.0), and dialyzed. The dialyzed product was adsorbed

TABLE 1

Reactivity with AGPRs from various animals

| Antibody No. | Human purified AGPR | | Mouse liver Extract with acetone powder | | Rat liver Extract with acetone powder | | Rabbit liver Extract with acetone powder | |
|---|---|---|---|---|---|---|---|---|
| | Unreduced | Reduced | Unreduced | Reduced | Unreduced | Reduced | Unreduced | Reduced |
| 30201 | + | + | + | + | + | + | + | + |
| 30202 | + | + | − | − | − | − | − | − |
| 30203 | + | − | − | − | − | − | − | − |
| 30204 | + | − | − | − | − | − | − | − |
| 30205 | + | + | − | − | − | − | − | − |
| 30206 | + | − | − | − | − | − | − | − |
| 30207 | + | − | − | − | − | − | − | − |
| 30208 | + | − | − | − | + | − | − | − |
| 30209 | + | − | − | − | − | − | − | − |
| 30210 | + | − | − | − | − | − | − | − |
| 30211 | + | + | + | + | + | + | + | + |
| 30212 | + | − | − | − | − | − | − | − |
| 30213 | + | − | − | − | − | − | − | − |
| 30214 | + | − | − | − | − | − | + | − |
| 30215 | + | − | − | − | − | − | − | − |
| 30216 | + | − | − | − | − | − | − | − |
| 30217 | + | − | − | − | − | − | − | − |
| 30218 | + | − | − | − | − | − | − | − |
| 30219 | + | − | − | − | − | − | − | − |
| 30220 | + | − | − | − | − | − | − | − |
| 30221 | + | − | − | − | + | + | − | − |
| 30222 | + | − | − | − | + | − | − | − |
| 30223 | + | − | − | − | + | − | − | − |
| 30225 | + | − | − | − | − | − | − | − |

Monoclonal antibodies were prepared by the limiting dilution method. Briefly, thymus cells of a BALB/c mouse were used as feeder cells and dispensed into the wells of a 96-well microculture plate ($10^6$ cells/0.2 ml well). Thereafter, a dilution of the hybridomas of the specific antibody-positive wells, which contained 10 cells per ml, was dispensed into each well of the microplate (0.1 ml/well). The media used were an HAT medium for the first dilution, an HT medium for the second dilution, and RPMI 1640 containing 15% FCS for the third and subsequent dilutions. The culture was incubated in a 5% $CO_2$ incubator at 37° C. for 10 days.

Selection of specific antibody-positive cells by ELISA and preparation of monoclonal antibodies by the limiting dilution method were each performed a total of three times. As a result, 24 strains of hybridomas that produced anti-AGPR monoclonal antibodies were obtained.

Referential Example 3
Isolation and Purification of Monoclonal Antibodies

The anti-AGPR monoclonal antibody-producing hybridomas obtained by the procedure described in Referential Example 2 were incubated within the abdominal cavity of a mouse, to thereby obtain monoclonal antibodies.

As a pretreatment, pristane (2,6-10,14-tetramethylpentadecane, 0.5 ml) was intraperitoneally administered to an 8-week-old BALB/c mouse. Eight days later, 4–15×$10^5$ cells of a hybridoma suspended in 0.5 ml of an RPMI 1640 medium were intraperitoneally administered to the mouse. From day 9 of administration, ascites was repeatedly collected and pooled. The collected ascites was onto a DEAE-Sephacel column which had been equilibrated with the same buffer, and was subsequently eluted in the same buffer with a linear gradient of 0–0.3M NaCl, to thereby obtain a purified antibody.

Referential Example 4
Selection of Combinations of Monoclonal Antibodies

From the purified monoclonal antibodies obtained in Referential Example 3, excepting antibodies that exhibited low color development values in the screening of Referential Example 2(3), antibodies that exhibited similar reactivities in Western blotting, and antibodies whose subclasses were γ2b, there were selected 30201, 30202, 30203, 30204, 30208, 30214, 30215, 30216, 30218, 30219, 30220, 30221, 30222, and 30225 as immobilized antibodies, and 30201, 30202, 30203, 30208, 30210, 30214, 30216, 30218, 30219, 30220, 30221, 30222, and 30225 as enzyme-labeled antibodies. ELISA was performed with these antibodies, and combinations suitable for the measurement of AGPR were selected. The antibodies were labeled with an enzyme in accordance with Referential Example 6 using purified IgG.

An antibody for preparing an immobilized phase was diluted with PBS so as to have a concentration of 2 µg/ml, dispensed in each well of a 96-well microplate at a ratio of 50 µl/well, and allowed to stand overnight at 4° C. The wells were washed three times with PBS (pH 7.2, BSA-PBS) containing 1% bovine serum albumin and 0.05% Tween 20. To each well of each plate, 50 µl of a 4-fold dilution of human serum or a 10-fold dilution of cell lysate of a human liver carcinoma cell strain were added, and reaction was allowed to proceed overnight at 4° C. Subsequently, washing was performed three times with PBS. Each of the enzyme-labeled monoclonal antibodies diluted to a 100-fold dilution with BSA-PBS was added in an amount of 50 µl, and reaction was allowed to proceed overnight at 4° C. The product of reaction was washed five times with PBS. Citric acid-phosphate buffer (pH 5.0) containing 11 mM orthophenylenediamine and 0.02% aqueous hydrogen peroxide solution was added thereto in an amount of 50 µl/well, to thereby cause a reaction. The reaction was allowed to proceed at room temperature for 30 minutes, and was subsequently stopped by the addition of 4.5M sulfuric acid in an amount of 50 µl/well. Absorption at 492 nm was measured. The results are shown in Tables 2 and 3.

were immobilized on a microplate made by NUNC Co. Briefly, the monoclonal antibodies 30220 were diluted in 50 mM carbonate buffer (pH 9.6) containing 150 mM NaCl so that the concentration of the antibodies became 2 µg/ml. The dilution was added to each well of the plate in an amount of 100 µl, and was then subjected to incubation at 4° C. for 3 hours. Subsequently, the solution was removed by aspiration. Phosphate buffer (pH 7.2) containing 1% BSA and 5% sucrose was added to each well in an amount of 300 µl. The wells were incubated at room temperature for 1 hour, and the resultant solution was removed by aspiration. The residue was brought to dryness in an Autodry desiccator at room temperature overnight, to thereby prepare an antibody-immobilized plate.

TABLE 2

| McAb | Reactivity with HepG2 cell lysate in respective McAb combinations HRP-labeled McAb | | | | | | | | | | | | |
|---|---|---|---|---|---|---|---|---|---|---|---|---|---|
| Coat | 01 | 02 | 03 | 08 | 10 | 14 | 16 | 18 | 19 | 20 | 21 | 22 | 25 |
| 01 | / | +++ | +++ | +++ | +++ | +++ | +++ | +++ | +++ | +++ | +++ | + | +++ |
| 02 | +++ | / | − | − | +++ | − | ++ | − | − | + | ++ | − | +++ |
| 03 | ++ | − | / | ++ | +++ | ++ | ++ | + | − | ++ | − | − | ++ |
| 04 | +++ | − | +++ | +++ | + | − | − | − | − | +++ | − | − | + |
| 08 | +++ | − | ++ | / | +++ | +++ | +++ | +++ | ++ | +++ | − | − | +++ |
| 14 | +++ | +++ | +++ | +++ | − | / | − | − | − | − | +++ | + | − |
| 15 | +++ | − | − | +++ | +++ | +++ | +++ | +++ | + | +++ | +++ | − | +++ |
| 16 | +++ | − | +++ | +++ | ++ | − | / | − | − | − | +++ | − | − |
| 18 | +++ | − | + | +++ | + | − | + | / | − | + | +++ | − | ++ |
| 19 | +++ | − | +++ | +++ | ++ | − | + | − | / | + | +++ | + | ++ |
| 20 | +++ | − | +++ | +++ | ++ | − | ++ | − | − | / | +++ | + | +++ |
| 21 | +++ | − | +++ | − | +++ | +++ | +++ | +++ | +++ | +++ | / | + | +++ |
| 22 | +++ | − | +++ | − | +++ | +++ | +++ | +++ | +++ | +++ | − | / | +++ |
| 25 | +++ | − | +++ | +++ | + | − | + | − | − | − | +++ | − | / |

1) Symbols "+++," "++," "+," and "−" indicate absorbances resulting from reactions with a 10-fold dilution of a HepG2 cell lysate by ELISA.
2) Absorbance was determined based on the difference between the data for a plate coated with McAb and that for the control (a plate coated with mouse IgG).
3) +++: >1.0 OD, ++: 0.5–1.0 OD, +: 0.2–0.5, −: <0.2, /: not measured.

TABLE 3

| McAb | Reactivity with human serum in respective McAb combinations HRP-labeled McAb | | | | | | | | | | | | |
|---|---|---|---|---|---|---|---|---|---|---|---|---|---|
| Coat | 01 | 02 | 03 | 08 | 10 | 14 | 16 | 18 | 19 | 20 | 21 | 22 | 25 |
| 01 | / | +++ | − | − | − | − | − | +++ | − | − | − | − | − |
| 02 | +++ | / | − | − | − | − | − | +++ | − | + | − | − | − |
| 03 | ++ | + | / | − | − | − | − | +++ | − | − | − | − | − |
| 04 | − | − | − | − | − | − | − | − | − | − | − | − | − |
| 08 | − | − | − | / | − | − | − | − | − | − | − | − | − |
| 14 | − | − | − | − | / | − | − | − | − | − | − | − | − |
| 15 | − | − | − | − | − | − | − | − | − | − | − | − | − |
| 16 | − | − | − | − | − | / | − | − | − | − | − | − | − |
| 18 | +++ | ++ | − | − | − | − | − | / | − | − | − | − | − |
| 19 | − | − | − | − | − | − | − | − | / | − | + | − | − |
| 20 | +++ | ++ | − | − | − | − | − | +++ | − | / | − | − | − |
| 21 | − | − | − | − | − | − | − | + | − | − | / | − | − |
| 22 | − | − | − | − | − | − | − | − | − | − | − | / | − |
| 25 | − | − | − | − | − | − | − | − | − | − | − | − | / |

1) Symbols "+++," "++," "+," and "−" indicate absorbances resulting from reactions with a 4-fold dilution of human serum by ELISA.
2) Absorbance was determined based on the difference between the data for a plate coated with McAb and that for the control (a plate coated with mouse IgG).
3) +++: >1.0 OD, ++: 0.5–1.0 OD, +: 0.2–0.5, −: <0.2, /: not measured.

Referential Example 5
Preparation of an Immobilized Plate

Anti-AGPR monoclonal antibodies (3020) purified according to the method described in Referential Example 3

Referential Example 6
Preparation of Enzyme-Labeled Antibodies

As an enzyme for labeling antibodies, horse radish peroxidase (HRP) was used. Labeling was performed in accordance with a method of Nakane et al. (Nakane et al., J. Histochem., 22:1084, 1974). Briefly, a 5 OD equivalent (based on the absorbance at 280 nm) of a fragment of F(ab')-fragmented 30201 monoclonal antibodies was dialyzed against 0.2M carbonate buffer (pH 9.5), to thereby concentrate its amount to approximately 1 ml using a collodion bag. HRP (5 mg) was dissolved in water (1 ml). Subsequently, 0.1M $NaIO_4$ (75 µl) was added thereto and the resultant mixture was stirred at room temperature for 20 minutes. The mixture was then dialyzed against 1 mM acetate buffer (pH 4.0), so as to decrease the pH to approximately 4. Subsequently, 0.2M Carbonate buffer (pH 9.5, 100 µl) was added to bring the pH to near 9. The mixture was mixed with the aforementioned monoclonal antibody solution and stirred at room temperature for 2 hours, to thereby effect labeling of F(ab') with HRP. The reaction was stopped by the addition of 4 mg/ml $NaBH_4$ (100 µl). Subsequently, $F(ab')_2$-HRP was purified via gel filtration using FPLC.

Example 1
Comparison of Reactivities Between Formulations

Reactivities were compared between the cases in which diluted specimen solutions and enzyme-labeled antibody solutions were as described in (1) to (4) below.

(1) Both the sample dilution and the enzyme-labeled antibody solution are formulation 1 (13 mM phosphate buffer that contained 1% BSA, 123 mM NaCl, and 0.05% Tween 20; pH 7.2);

(2) The sample dilution is formulation 2 (100 mM phosphate buffer that contained 2% BSA, 150 mM NaCl, and 0.05% Tween 20; pH 6.2), and the enzyme-labeled antibody solution are formulation 3 which does not contain phenol (20 mM BES buffer that contained 0.1% BSA, 150 mM NaCl, and 0.05% Tween 20; pH 7.0);

(3) The sample dilution is formulation 1, and the enzyme-labeled antibody solution is formulation 1 which contains phenol (13 mM phosphate buffer that contained 0.1% BSA, 123 mM NaCl, 0.05% Tween 20, and 0.1% phenol; pH 7.2); and (4) The sample dilution is formulation 2, and the enzyme-labeled antibody solution is formulation 3 which contains 0.1% phenol.

Briefly, purified AGPR was diluted with each of the above buffers so that the AGPR concentrations of 25, 12.5, 5, and 2.4 ng/ml were obtained. The dilutions were added in wells of the immobilized plate prepared in Referential Example 5 (200 µl/well), and reaction was allowed to proceed at room temperature overnight. After three washings with PBST, an enzyme-labeled antibody diluted with each buffer so that absorbance at 280 nm was 1 mOD was added to each well in an amount of 100 µl, to thereby cause a reaction at room temperature for 1 hour. After five washings with PBST, 100 µl of a substrate solution (citrate buffer that contained 11 mM orthophenylenediamine and 0.02% hydrogen peroxide; pH 5.0) were added to each well. Reaction was allowed to proceed at room temperature for 10 minutes. Subsequently, 1.5N sulfuric acid was added to each well in an amount of 100 µl. Absorbance at 492 nm was measured using a microplate reader. The results are shown in FIG. 1.

Figure 1:
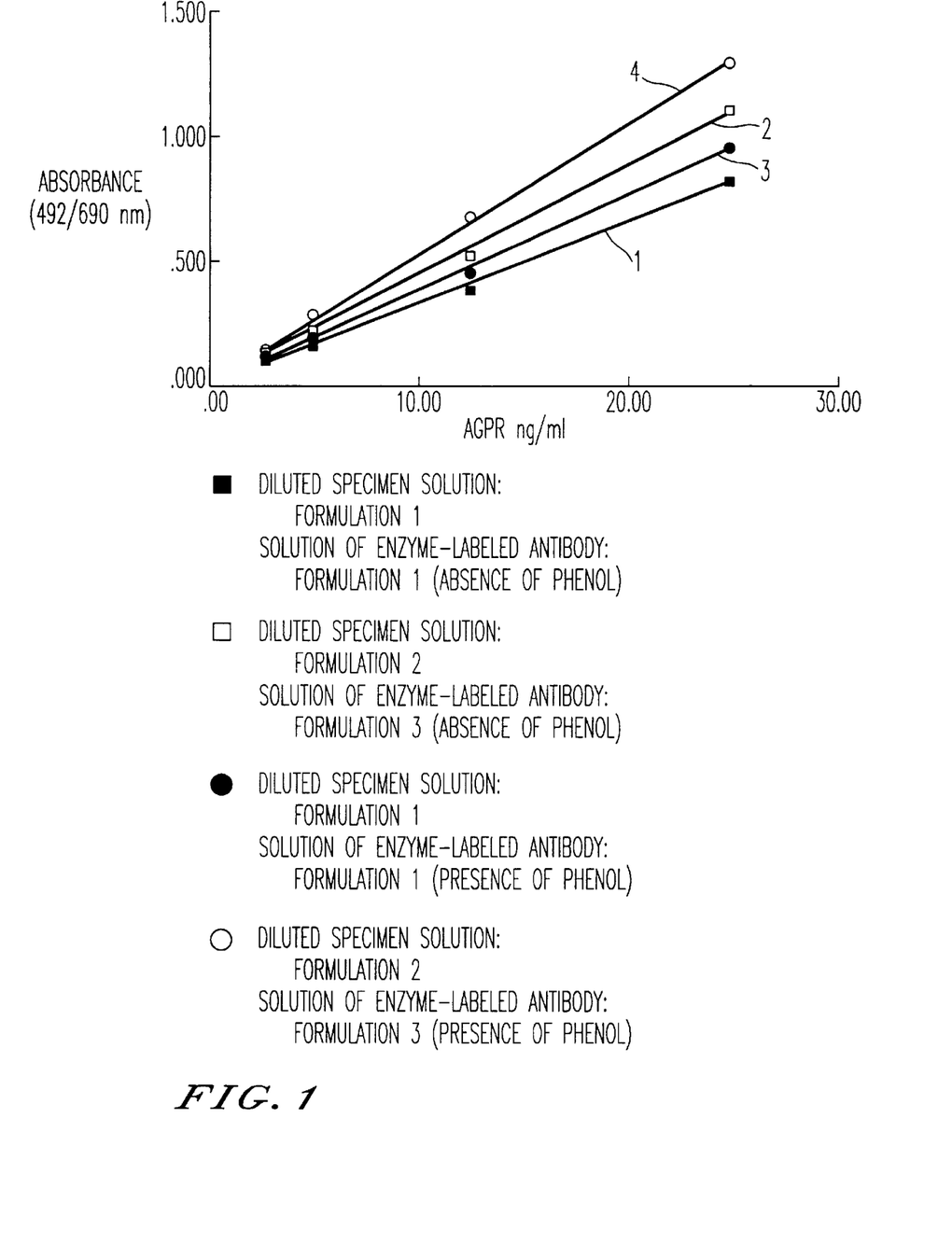
FIG. 1 is a graph showing difference in reactivity when pH is changed in the presence or absence of phenol.

As is apparent from FIG. 1, it is possible to measure the concentration of AGPR with higher sensitivity when the pH of a diluted specimen solution is 6.2 and/or an enzyme-labeled antibody solution contains phenol.

Example 2
Reproducibility of Within-Run and Between-Run

Reproducibility of within-run and between-run of the assay system of the present invention were determined for an assay in which were used serums at different concentrations that were diluted to 4-fold dilutions, the immobilized plate prepared in Referential Example 5, diluted specimen solutions (100 mM phosphate buffer that contained 2% BSA, 150 mM NaCl, and 0.05% Tween 20; pH 6.2), and a solution containing an enzyme-labeled antibody whose absorbance at 280 nm was 1 mOD (20 mM BES buffer that contained 0.1% BSA, 150 mM NaCl, 0.05% Tween 20, and 6.1% phenol; pH 7.0). Briefly, each of the serum samples having different concentrations was diluted to a 4-fold dilution, and a 200 µl aliquot thereof was added to each well. Reaction was allowed to proceed overnight at room temperature. The subsequent procedure was identical to that described in Example 1. The results of reproducibility of within-run and between-run are shown in Table 4. Dispersions, which varied in accordance with the concentrations of AGPR, were 4–14% and 7–14%, respectively.

TABLE 4

| Accuracy of the ELISA for AGPR | | | |
|---|---|---|---|
| | highest | intermediate | lowest |
| Within assay (n = 10) | | | |
| Mean AGPR (µg/l) | 20.1 | 6.7 | 2.1 |
| SD (µg/l) | 0.9 | 0.5 | 0.3 |
| CV (%) | 4.6 | 7.3 | 13.6 |
| Between assay (n = 5) | | | |
| Mean AGPR (µg/l) | 19.6 | 7.1 | 2.1 |
| SD (µg/l) | 1.5 | 0.6 | 0.3 |
| CV (%) | 7.8 | 8.9 | 13.1 |

Example 3
Addition-and-Recovery Test

In a manner similar to that described in Example 2, a recovery test was performed on the present assay system in which each of serum samples to which purified AGPR was added at different concentrations was diluted to a 4-fold dilution,. The results are shown in Table 5. The recovery ratio was between 93 and 99%.

TABLE 5

| Recovery test AGPR (ug/l) | | | |
|---|---|---|---|
| Added | Observed | Expected | Recovery (%) |
| 0 | 0.2 | | |
| 2 | 2.1 | 1.9 | 95 |
| 7 | 6.7 | 6.5 | 93 |
| 20 | 20.1 | 19.9 | 99 |

Example 4
Phenol Addition Test

An AGPR solution which had been diluted to a concentration of 12.5 ng/ml with the diluted specimen solution (formulation 2) used in Example 1 was added to each well (200 µl/well) of the immobilized plate prepared in Referential Example 5, to thereby cause a reaction at room temperature for overnight. The product of reaction was washed three times with PBST. Phenol at different concentrations (0%, 0.01%, 0.05%, and 0.1%) was added to each well in combination with an enzyme-labeled antibody solution whose absorbance at 280 nm was 1 mOD (100 µl/well). Reaction was allowed to proceed at room temperature for 1 hour. The subsequent procedure was identical to that described in Example 1. The results are shown in Table 6.

TABLE 6

| Phenol | 12.5 ng/ml | Blank | Gross | (%) |
|---|---|---|---|---|
| 0.1% | 1.116 | 0.013 | 1.103 | 115.8% |
| 0.05% | 1.089 | 0.012 | 1.077 | 113.1% |
| 0.01% | 1.093 | 0.013 | 1.080 | 113.4% |
| 0.001% | 1.015 | 0.012 | 1.003 | 105.3% |
| (−) | 0.963 | 0.011 | 0.952 | 100.0% |

The values indicate absorbance.

Example 5
AGPR Assay After Hepatectomy

Figure 2:
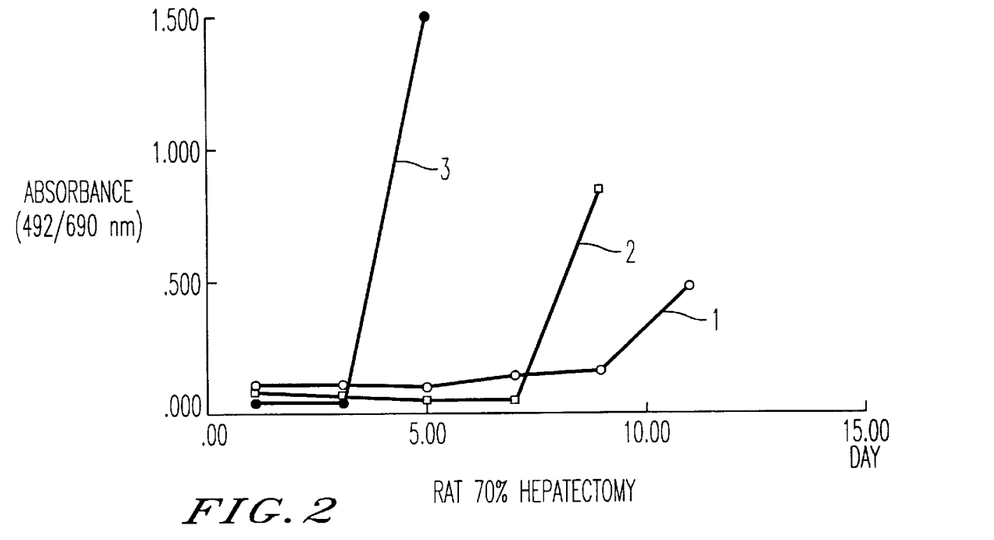
FIG. 2 is a graph showing changes in AGPR after hepatectomy.

In a manner similar to that described in Referential Example 5, 4-fold dilutions of serum samples obtained from a rat that had undergone hepatectomy of 70% excision of the liver were tested using a plate having thereon immobilized 30208-monoclonal antibodies reacting with rat and human AGPR, a diluted specimen solution (100 mM phosphate buffer that contained 2% BSA, 150 mM NaCl, and 0.05% Tween 20; pH 6.2) and an enzyme-labelled antibody solution whose absorbance at 280 nm was 1 mOD (20 mM BES buffer that contained 0.1% BSA, 150 mM NaCl, 0.05% Tween 20, and 0.1% phenol). The rat that received hepatectomy grew favorably. The assay procedure was similar to that described in Example 2. The results are shown in FIG. 2.

Among the rats that progressed favorably exhibited elevation in AGPR (in FIG. 2, indicated by numeral 3), which was considered to reflect the liver regeneration.

Example 6
AGPR Assay of Liver Disease Specimens

Serum samples from healthy subjects (238 cases), alcoholic hepatocirrhosis (9 cases), viral hepatocirrhosis (19 cases), and viral chronic active hepatitis (23 cases) were assayed for the concentration of AGPR. The assay method described in Example 2 was used. The results are shown in Table 7.

TABLE 7

Serum AGPR concentrations represented by percentile measured for patients suffering from viral hepatitis and alcoholic hepatocirrhosis

|  | Median | 90% tile |
|---|---|---|
| Healthy subjects (n = 238) | 0.4 ng/ml | 2.4 ng/ml |
| Alcoholic hepatocirrhosis (n = 9) | 2.9 | 5.7 |
| Viral hepatocirrhosis (n = 19) | 0.7 | 2.6 |
| Viral chronic active hepatitis (n = 23) | 0.5 | 2.9 |

The results shown in Table 7 demonstrate that the serum from alcoholic hepatocirrhosis exhibited an elevated AGPR concentration.

Example 7
AGPR Assay in a Supernatant of a Liver Cell Culture

Figure 3:
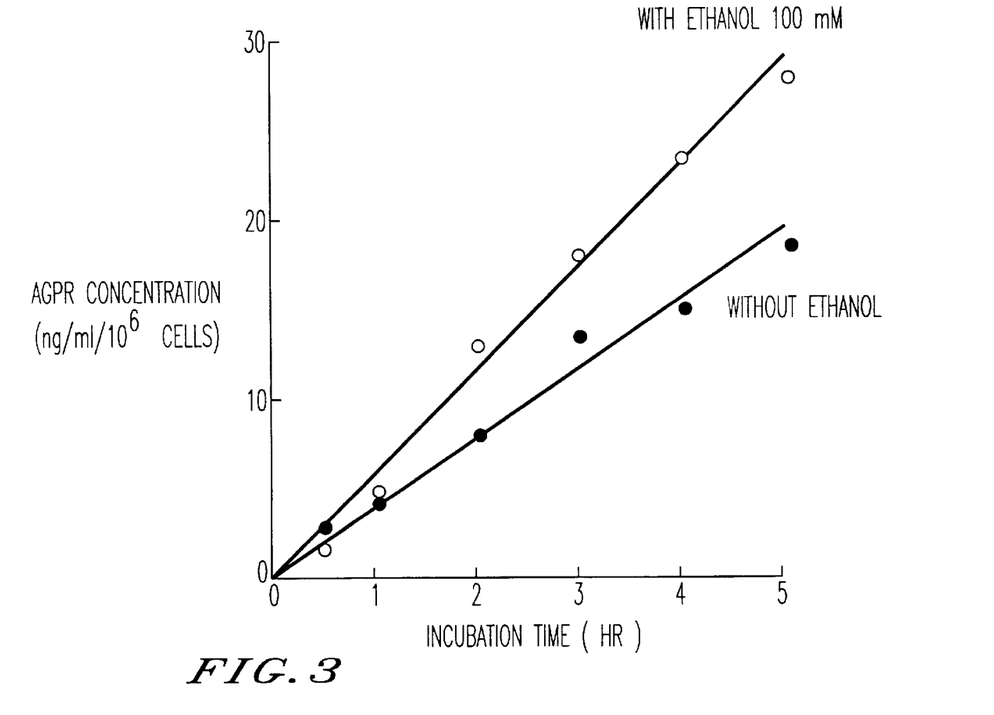
FIG. 3 is a graph showing changes in AGPR in supernatants of liver cell cultures.

A human liver carcinoma cell strain (HepG2) was incubated in a petri dish that contained an MEM medium supplemented with 10% FCS. When the cells reached confluency, the supernatant of the culture was removed, and the cells were washed with an MEM medium. The washed cells were incubated at 37° C. in the presence or absence of ethanol (100 mM). After certain periods of time (0.5, 1, 2, 3, 4, and 5 hours after incubation), the amount of AGPR in the culture supernatant (200 µl) was measured. The procedure described in Example 2 was used for assaying the antigens after reaction. The results are shown in FIG. 3.

INDUSTRIAL UTILITY

When the assay method for AGPR of the present invention is used, AGPR can be assayed with high sensitivity and improved accuracy.

Therefore, the method of the present invention is useful for grasping the state of liver cells, and particularly for grasping and detecting various aspects associated with hepatectomy with ease, including the status of liver regeneration, alcoholic liver disorders, fluidity of liver cell membranes induced by in vitro drug stimulation, and changes in liver cell mechanisms reflected by changes in turnover of liver cell membranes.

We claim:

1. A method for detecting the asialoglycoprotein receptor in a sample, comprising:
   (a) contacting the sample, at a pH from 5 to 7, with an unlabeled antibody which is capable of binding the asialoglycoprotein receptor; and
   (b) contacting the sample from step (a) with a composition comprising an antibody which is capable of binding the asialoglycoprotein receptor and is labeled with an enzyme.

2. The method of claim 1, wherein detection of the asialoglycoprotein receptor is enhanced by contacting the unlabeled antibody with the sample at the pH from 5 to 7 in step (a) as compared to contacting the unlabeled antibody and the sample at pH 7.2.

3. The method of claim 1, wherein the unlabeled antibody is immobilized.

4. The method of claim 1, wherein the pH in step (a) is 5.5 to 6.5.

5. A method for detecting the asialoglycoprotein receptor in a sample, comprising:
   (a) contacting the sample with an unlabeled antibody which is capable of binding the asialoglycoprotein receptor; and
   (b) contacting the sample from step (a) with a composition comprising phenol and an antibody which is capable of binding the asialoglycoprotein receptor and is labeled with an enzyme, wherein the phenol accelerates the binding of the antibody which is capable of binding the asialoglycoprotein receptor and the asialoglycoprotein receptor.

6. The method of claim 5, wherein detection of the antibody is enhanced by the presence of the phenol in step (b) as compared to conducting step (b) in the absence of the phenol.

7. The method of claim 5, wherein the concentration of phenol in step (b) is 0.001 to 0.2%.

8. The method of claim 5, wherein the concentration of phenol in step (b) is 0.01% to 0.1%.

9. The method of claim 5, wherein the unlabeled antibody is immobilized.

10. A method for detecting the asialoglycoprotein receptor in a sample, comprising:
    (a) contacting the sample, at a pH from 5 to 7, with an unlabeled antibody which is capable of binding the asialoglycoprotein receptor; and
    (b) contacting the sample from step (a) with a composition comprising phenol and an antibody which is capable of binding the asialoglycoprotein receptor and is labeled with an enzyme.

11. The method of claim 10, wherein detection of the asialoglycoprotein receptor is enhanced by contacting the unlabeled antibody with the sample at the pH from 5 to 7 in step (a) as compared to contacting the unlabeled antibody and the sample at pH 7.2 and by the presence of the phenol in step (b) as compared to conducting step (b) in the absence of the phenol.

12. The method of claim 10, wherein the unlabeled antibody is immobilized.

13. The method of claim 10, wherein the pH in step (a) is 5.5 to 6.5.

14. The method of claim 10, wherein the concentration of phenol in step (b) is 0.001 to 0.2%.

15. The method of claim 10, wherein the concentration of phenol in step (b) is 0.01% to 0.1%.

* * * * *